Sept. 17, 1974 F. W. ANDERSON Plant Pat. 3,618
PLUM TREE
Filed Aug. 16, 1973
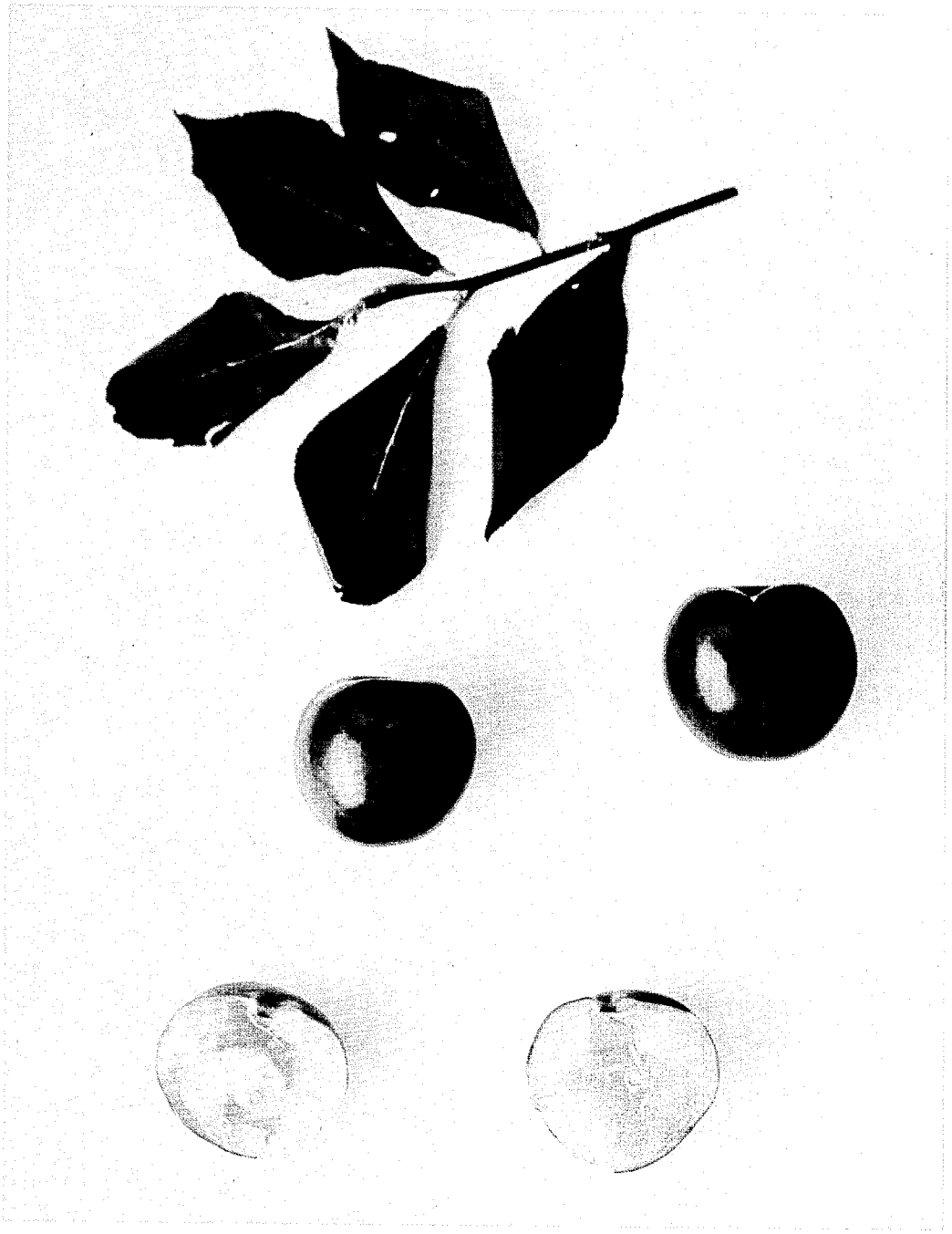

United States Patent Office

Plant Pat. 3,618

Patented Sept. 17, 1974

3,618

PLUM TREE

Frederic W. Anderson, Merced, Calif., assignor to Reedley Nursery, Inc., Reedley, Calif.

Filed Aug. 16, 1973, Ser. No. 388,976

Int. Cl. A01h 5/03

U.S. Cl. Plt.—38 1 Claim

ABSTRACT OF THE DISCLOSURE

A plum tree which is large, vigorous, upright to spreading, foliated with large to medium size obovate leaves, and a productive bearer of uniform, large to medium size, globose, clingstone fruit having red skin and bistre green flesh.

*Background of the Variety*: Over a substantial number of years I have engaged in an extensive and continuing plant breeding program at my experimental nursery and orchard located near Le Grand, Merced County, Calif.; one purpose of such program being to provide improved varieties of fruit trees. The present variety of plum tree resulted from my endeavors in the conduct of such plant breeding program.

*Origin of the Variety*: The present variety of plum tree was originated by me, in my experimental nursery and orchard located as aforesaid, as an open-pollinated seedling of the Red Beaut (U.S. Plant Pat. No. 2,539).

*Asexual Reproduction of the Variety*: Upon recognition by me of the new and distinct characteristics of the present variety of plum tree, I asexually reproduced it by grafting on mature orchard trees in my said experimental orchard, and, in maturity, such reproductions ran true to the original tree in all respects.

*Summary of the Variety*: The present variety of plum tree is large, vigorous, upright to spreading, foliated with large to medium size obovate leaves, and a productive bearer of uniform, large to medium size, globose, clingstone fruit having red skin and bistre green flesh; the variety—which in general resembles the Red Beaut—being, in comparison, essentially characterized, as to novelty, by fruit which is somewhat larger, more nearly round in shape, brighter red in exterior color, and ripens about three to five days later.

*Brief Description of the Drawing*: The drawing is an illustration, by photographic reproduction in color, of a twig with leaves, and separate fruit; one of the latter being cut in half with the stone remaining in one half.

*Description of the Variety*: The botanical details of this new and distinct variety of plum tree—with color definitions (except those in common color terms) referenced to Maerz and Paul Dictionary of Color—are as follows:

Tree:
- *Size.*—Large.
- *Vigor.*—Vigorous.
- *Growth.*—Upright to spreading.
- *Production.*—Productive.

Trunk:
- *Size.*—Medium.
- *Texture.*—Medium.

Branches:
- *Size.*—Medium.
- *Texture.*—Medium.
- *Lenticels.*—Number: Medium. Size: Medium.

Leaves:
- *Size.*—Large to medium. Average length—3½". Average width—1¾".
- *Form.*—Obovate. Acutely pointed.
- *Thickness.*—Medium.
- *Texture.*—Smooth.
- *Margin.*—Crenate.

- *Petiole.*—Medium length. Medium thickness.
- *Glands.*—Average number—2. Alternate. Globose. Usually positioned 2 on petiole, often 1 or 2 on base of blade.
- *Color.*—Top side—Medium green (22–I–9). Under Side—Lighter green (22–K–7).

Flower buds:
- *Length.*—Short.
- *Form.*—Obtuse. Plump.

Flowers:
- *Blooming Period.*—About 2 days before Santa Rosa (unpatented). Early, as compared with other varieties.
- *Color.*—White.

Fruit:
- *Maturity When Described.*—Eating ripe—June 10th, 1973.
- *Date of First Picking.*—June 4th, 1973.
- *Date of Last Picking.*—June 10th, 1973.
- *Size.*—Uniform. Large to medium. Average diameter axially—2⅛". Average transversely in suture plane—2".
- *Form.*—Uniform. Globose.
- *Suture.*—Shallow. Extends from base to apex on ventral side.
- *Ventral Surface.*—Rounded slightly.
- *Cavity.*—Rounded.
- *Base.*—Rounded.
- *Apex.*—Short.

Skin:
- *Thickness.*—Medium.
- *Texture.*—Tough.
- *Tendency To Crack.*—None noted.
- *Down.*—Wanting.
- *Color.*—Red (56–L–12).

Flesh:
- *Texture.*—Firm. Crisp. Melting.
- *Fibers.*—Few.
- *Ripens.*—Evenly.
- *Flavor.*—Sub-acid. Delicate.
- *Eating Quality.*—Good.
- *Color.*—Bistre green (13–L–5).

Stone:
- *Type.*—Cling.
- *Size.*—Medium to small. Average length—⅝". Average breadth—½". Average thickness—¼".
- *Color.*—Beige (13–H–7).

Use: Market. Dessert.

Keeping Quality: Good.

Resistance to insects and diseases: No unusual susceptibilities noted.

Shipping quality: Good.

The plum tree and its fruit herein described may vary in slight detail due to climatic and soil conditions under which the variety may be grown; the present description being of the variety as grown in the Central Valley of California.

I claim:

1. A new and distinct variety of plum tree, substantially as illustrated and described, which is large, vigorous, upright to spreading, foliated with large to medium size obovate leaves, and a productive bearer of uniform, large to medium size, globose, clingstone fruit having red skin and bistre green flesh; the fruit of the variety, in comparison to the Red Beaut, being somewhat larger, more nearly round in shape, brighter red in exterior color, and ripening about three to five days later.

No references cited.

ROBERT E. BAGWILL, Primary Examiner